(12) United States Patent
Messier (10) Patent No.: US 9,777,413 B2
(45) Date of Patent: Oct. 3, 2017

(54) COMPRESSION KNITTED ARTICLE

(71) Applicant: Robert H. Messier, Raleigh, NC (US)

(72) Inventor: Robert H. Messier, Raleigh, NC (US)

(*) Notice: Subject to any disclaimer, the term of this patent is extended or adjusted under 35 U.S.C. 154(b) by 361 days.

(21) Appl. No.: 14/459,255

(22) Filed: Aug. 13, 2014

(65) Prior Publication Data
US 2015/0051524 A1    Feb. 19, 2015

Related U.S. Application Data

(60) Provisional application No. 61/865,396, filed on Aug. 13, 2013.

(51) Int. Cl.
*D04B 9/52* (2006.01)
*A61F 13/08* (2006.01)

(52) U.S. Cl.
CPC ............. *D04B 9/52* (2013.01); *A61F 13/08* (2013.01)

(58) Field of Classification Search
CPC ............. A61F 13/08; D04B 9/52; D04B 1/26
See application file for complete search history.

(56) References Cited

U.S. PATENT DOCUMENTS

| | | | | |
|---|---|---|---|---|
| 2,841,971 A * | 7/1958 | Bird | ............... | A41B 11/00 66/178 A |
| 2,962,885 A * | 12/1960 | Knohl | ............... | D04B 1/265 66/171 |
| 3,064,456 A * | 11/1962 | Bird | ............... | A61F 13/08 66/178 A |
| 3,889,494 A * | 6/1975 | Patience | ............... | D04B 1/265 66/178 R |
| 3,975,929 A * | 8/1976 | Fregeolle | ............... | D04B 1/265 2/239 |
| 4,027,667 A * | 6/1977 | Swallow | ............... | D04B 9/52 2/240 |
| 4,048,818 A * | 9/1977 | Cueman | ............... | D04B 1/265 66/172 E |
| 4,086,790 A * | 5/1978 | Hanrahan, Jr. | ............... | D04B 1/265 66/178 A |
| 4,172,456 A * | 10/1979 | Zens | ............... | A61F 13/08 2/240 |
| 4,180,065 A * | 12/1979 | Bowen | ............... | A61F 13/08 2/239 |
| 4,198,834 A * | 4/1980 | Reid, Sr. | ............... | A61F 13/085 66/172 E |
| 4,502,301 A * | 3/1985 | Swallow | ............... | A61F 13/08 602/62 |
| 4,527,402 A * | 7/1985 | Swallow | ............... | A61F 13/08 2/239 |
| 4,561,267 A * | 12/1985 | Wilkinson | ............... | A41B 11/00 66/172 E |

(Continued)

*Primary Examiner* — Danny Worrell
(74) *Attorney, Agent, or Firm* — Tracey S. Truitt; Armstrong Teasdale LLP (57) ABSTRACT

The present disclosure provides a compression hosiery designed to be worn on a human leg. The compression hosiery includes a first portion adapted for a lower portion of a human leg and having a first pressure gradient slope and a second portion adapted for an upper portion of a human leg and having a second pressure gradient slope. The pressure gradient slopes generally decrease in a direction from the first portion to the second portion such that the compressive forces at the first portion are greater than the compressive forces at the second portion when the hosiery is worn.

19 Claims, 4 Drawing Sheets

(56) References Cited

U.S. PATENT DOCUMENTS

| | | | | |
|---|---|---|---|---|
| 6,216,495 B1* | 4/2001 | Couzan | ............... | A61F 13/08 |
| | | | | 2/239 |
| 7,043,329 B2* | 5/2006 | Dias | ............... | D04B 7/32 |
| | | | | 66/55 |
| 7,192,411 B2* | 3/2007 | Gobet | ............... | A41B 11/003 |
| | | | | 2/239 |
| 7,895,863 B2* | 3/2011 | Smith | ............... | A61F 13/08 |
| | | | | 66/172 E |
| 8,317,736 B2* | 11/2012 | Virkus | ............... | A61F 13/08 |
| | | | | 2/240 |
| 2016/0076175 A1* | 3/2016 | Rock | ............... | D04B 1/18 |
| | | | | 66/171 |

* cited by examiner

COMPRESSION KNITTED ARTICLE

RELATED APPLICATIONS

The present application claims the priority benefit of provisional application Ser. No. 61/865,396, filed Aug. 13, 2013, the teachings and content of which is incorporated by reference herein.

BACKGROUND OF THE INVENTION

1. Field of the Invention

The present invention relates generally to hosiery, and more particularly, to a knitted compression article for improved vascular health.

2. Description of the Prior Art

Prior art compression hose are designed as support devices worn on the legs, and used to compensate for the widely-incurred and age-related biologic deterioration of blood return from the legs. Consistent with physiologic patterns throughout the human body, the legs receive blood via the arterial system, and return it through the venous channels back to the heart. The ubiquitous exit vessels (veins) are comprised in a coupled parallel arrangement, termed the superficial and deep systems. The two systems communicate via venous perforators, which arrange themselves similar to a scaffold. Within the lumen of the superficial system (called the greater and lesser saphenous veins, residing in front and behind the leg respectively) there exists a tiny assemblage of one-way valves. These function to orchestrate a through passage of blood such that after flowing arterially to the soft tissues of the leg and distally to the feet, effluent venous drainage is continuously collected in the superficial venous system(s), routed via perforators to the central deep system (not visible externally and residing nearer the central core of the leg) and directed back to the heart. There are also valves within the deep system. Working responsively with the squeezing and relaxing leg muscles which compress the intervalvular venous segments, the valves maintain return as a one-way process with the majority of the venous blood flowing in response to this muscular contraction. When the legs are at rest, normal (competent) valves close and forward motion ebbs, but backflow is prevented. With leg activity and muscular contraction, the veins are squeezed by the leg muscles causing the valves to open and facilitate forward blood return through communicating branches to the parallel deep system, and thence to the heart.

Unfortunately, with the development of the common pathologic condition addressed herein and termed "valvular incompetence," this physiologic one-way functionality degenerates. When the valves lose competence, they are unable to prevent blood flow back toward the feet. This problem is exacerbated by prolonged sitting or standing situations where gravity also encourages backflow. Progressively, the superficial system (visible externally) sustains debilitative venous hypertension and stasis, leading to tissue edema, varicosity formation and other damaging sequellae. Compression hosiery garments are designed to substitute for the incompetent superficial venous valve function, and rectify the resultant pooling tendencies by coercing the transference of venous blood from this impaired superficial system into the deep system. This is achieved through the external application of a longitudinally graduated and centrally-directed radial force. The superficial venous distension is thereby retarded, blood pooling minimized and venous stasis consequences subdued.

While compression stockings as in the prior art are widely used and do reliably mitigate this superficial venous hypertension, a regimen of multi-hour or all-day wear is typically required. Most users resist wearing prior art compression stockings for extended and possibly chronic periods, largely because of an attendant discomfort. In the prior art, a cephalad blood flow trajectory is reinstated with a crude compression gradient which decreases linearly from ankle to groin. The garments are usually marketed in either knee-high or thigh-high options, the latter generally recommended for the more severe cases of venous stasis. As such, this prior art compression hosiery is imperfectly designed with respect to certain important anatomic features, and these design elements likely contribute to the attendant discomfort. An average set of compression hosiery consists of a 40 mmHg radial force applied at the ankle, with a linear 70% reduction to the top of the garment that may extend either to the knee or to the thigh. The uniform gradient slope of the prior art compression, is conceptually inconsistent with the normal anatomic pattern of the venous valves intended to be compensated for. While studies are few, it has been shown that the numeric density of the valve system below the knee (5-7 valves) is very different from that above the knee (approx. 3 valves). Because the superficial venous valves are numerically more populous below the knee than above, the force vector imparted is more vigorously structured between ankle and knee (calf) than between knee and groin (thigh). Additionally, the lower leg musculofascial architecture is denser than that of the thigh, bringing about an augmented relationship of the veins with the propulsive muscles. More importantly, current knee-high design sharply ends compression just below the tibial plateau, where the superficial system insinuates deeply and among the ligaments and bony prominences of the knee joint complex. Wearers of knee-high compression hosiery almost universally note a very uncomfortable constrictive effect at that point.

Both the failure of compression hosiery design to recapitulate the inherent differences between the below knee and above knee anatomy, and the common knee high design pattern of ending at the tibial plateau, likely reduce garment efficacy and wearer comfort. Inappropriately high thigh compression is unpleasant and may actually retard venous return; inadequate calf gradients are likely ineffective, and straight-line compression declination mandates one or both of these conditions. There remains, therefore, a need for attractively-patterned, medically functional compression hosiery that restores the one-way valvular effects through appropriate compression gradient slopes which respect the nonlinear valvular cadence throughout the human leg. In addition, structural avoidance of the constrictive effect at the tibial plateau will lend itself to increased patient compliance.

Examples of relevant documents from the prior art include: U.S. Pat. No. 5,989,948 describes a support sock made of elastomeric material and designed to enhance athletic performance, including a sock with a pressure gradient with the maximum pressure exhibited at the foot portion and a minimum pressure at the proximal end, as well as a distinct foot portion of the sock and biomechanical supports to stabilize muscle and tendon groups during activity; U.S. Pat. Nos. 6,572,574 and 6,371,933, and US Patent Application Publication No. 20020029012 for a compressive orthosis of the sock type for treating circulatory disease of the lower limbs, in particular for applying compressive support to the leg after venous ulcer, which teaches an orthosis designed to apply graduated compression beginning with the greatest pressure at the foot or ankle, including a sock with a leg portion made of knitted compression material; US Patent Application Publication No. 20080171959 for a compression article, particularly a compression stocking with a surface pattern, describes a compression stocking or tights made of elastic knitted fabric, wherein additional knitting is done to obtain a surface pattern including chessboards, stripes, argyle, bubble or circles.

Other references exemplary of prior art compression stockings include: U.S. Pat. Nos. 7,441,419, 7,117,695, 6,725,691, 6,613,007, 6,572,437, and 6,216,495.

While compression articles like these are known in the art, and surface patterned knitting is known, the combination fails to deliver compression gradients that simulate the body's valve-based system from foot toward the knee area, and from thence to the thigh, and therefore fail to perform or function in a manner that replicates it. In addition, there are few commercially available knee-high style garments that continue their compression to some level above the knee, thereby avoiding the constrictive effect at the tibial plateau. Thus, there remains a need in the art for compression knitted articles for application in lower leg (knee high) to total leg (thigh high) coverage, which simulate the inhomogeneous venous valve distribution through a nonlinearly sloped pressure gradient, maintains compression cephalad to the knee joint at a physiologic gradient slope in both the knee high and thigh high versions.

SUMMARY OF THE INVENTION

The present disclosure overcomes the problems inherent in the prior art and provides a compression hosiery for improved vascular health. In one aspect of the present disclosure, the compression hosiery includes a wearable article having a physiologic pressure gradient profile specifically proportional to valve population density and generally to the gross anatomic feature of the bony knee joint. As such, the compression gradient possesses a steeper slope from ankle to the knee than from knee to the thigh, and thereby recapitulates the biphasic valve density. In general, the pressure gradient slope (mmHg/inch) between the ankle and just above the tibial plateau of the knee ranges from 5.4:1 to 2.2:1, including slopes of 5.4:1, 5.3:1, 5.2:1, 5.1:1, 5:1, 4.9:1, 4.8:1, 4.7:1, 4.6:1, 4.5:1, 4.4:1, 4.3:1, 4.2:1, 4.1:1, 4:1, 3.9:1, 3.8:1, 3.7:1, 3.6:1, 3.5:1, 3.4:1, 3.3:1, 3.2:1, 3.1:1, 3:1, 2.9:1, 2.8:1, 2.7:1, 2.6:1, 2.5:1, 2.4:1, 2.3:1, and 2.2:1. For compression hosiery that extends beyond the tibial plateau, the slope of the pressure gradient is generally less than that below the tibial plateau. In general, the pressure gradient has a slope of 2.8:1 or less including slopes of 2.7:1, 2.6:1, 2.5:1, 2.4:1, 2.3:1, 2.2:1, 2.1:1, 2:1, 1.9:1, 1.8:1, 1.7:1, 1.6:1, 1.5:1, 1.4:1, 1.3:1, 1.2:1, and 1.1:1. As can be seen, the slopes have some overlap. In preferred forms, the slope between the ankle and tibial plateau and between the tibial plateau and hip will be different with the pressure gradient being higher for the lower leg than the upper leg. It is also contemplated that multiple slopes will be present in a compression hosiery, thereby forming multiple compression zones. Such a hosiery can be customized for a particular individual, taking into account characteristics such as their particular anatomy including valvular location and physical size of their leg. In embodiments having multiple compression zones of varying slope, it is preferred to have more compression zones in the calf portion of the hosiery than in the thigh portion of the hosiery. Again, this is to recapitulate the natural valvular anatomy. In preferred forms, the pressure gradient slope will generally decrease from the lower leg to the upper leg. For example, a compression hosiery could provide a pressure gradient slope of 4.3:1 in the lower calf, 3.5:1 in the upper thigh, 3:1 just above the tibial plateau, 2.3:1 in the lower thigh, and 1.9:1 in the upper thigh. In one preferred embodiment, the ratio of slopes (mmHg/inch) should approach 3:1 in the portion below the tibial plateau and 2:1 above the tibial plateau. Additionally, in the knee high version, the garment would end above the tibial plateau (knee) maintaining compression throughout the joint. In other preferred embodiments as well as many described herein, the gradient slope employed in the compression hosiery will be non-linear and will be reflective of the valve numbers existing in the upper and lower leg.

With respect to the pressures, pressures between 5 mm Hg and 60 mm Hg are contemplated in the present disclosure. Higher and lower pressures are usable, but such pressures have little or no beneficial clinical effect. Accordingly, in one embodiment, the pressures in the portion of the compression hosiery below the tibial plateau are between 60 mm Hg and 20 mm Hg and the pressures in the portion of the compression hosiery above the tibial plateau are between 25 mm Hg and 5 mm Hg. It is understood that the pressures of any particular hosiery can be designed to have specific pressure gradients that are customized for a particular individual. In one preferred embodiment, the pressure at the ankle is about 30 mm Hg, decreasing to about 13 mm Hg at the tibial plateau and then decreasing to about 8 mm Hg just below the hip. In another preferred embodiment, the pressure at the ankle is about 38 mm Hg decreasing to about 13 mm Hg at the tibial plateau and then decreasing to about 6.5 mm Hg just below the hip. In yet another preferred embodiment, the compression hosiery includes multiple compression zones above and below the tibial plateau. For example, one compression zone extends from the ankle for several inches, a second compression zone extends upwardly toward the knee for several more inches, a third compression zone extends from the termination of the second zone to the tibial plateau, a fourth compression zone extends from the tibial plateau to the mid-thigh area, and a fifth compression zone extends from the mid-thigh area to the upper thigh area. Potential pressures in the first zone decrease from 42 mm Hg to 28 mm Hg, from 28 mm Hg to 19 mm Hg in the second zone, from 19 mm Hg to 14 mm Hg in the third zone, from 14 mm Hg to 9 mm Hg in the fourth zone, and from 9 mm Hg to 7 mm Hg in the fifth zone.

A second aspect of the present disclosure is to provide the methods for making the described compression hosiery for improved vascular health including a knitted article having graduated compression density that simulates human valve distribution in the legs. In general, the methods of the present invention will comprise an apparatus for forming a compression hosiery article that has a generally decreasing pressure gradient slope from the toe portion to the knee or thigh portion. In preferred forms, the apparatus will be able to form articles that have multiple zones of compression from the ankle to the knee or thigh area. In particularly preferred forms, the apparatus will be capable of forming the compression hosiery described herein. It would also include the methods for retaining compression at the level of the knee.

A third aspect of the disclosure provides methods of using the compression hosiery described herein to improve blood return from the legs and avoid problems associated with valvular incompetence. In one embodiment of this aspect, an individual will don an article of compression hosiery as described herein. The blood return from the legs of such an individual will be improved as a result of the compressive forces provided by the hosiery.

In a fourth aspect, the present disclosure provides a knitted article comprising a tubular body having a closed first end and an open second end connected by an intervening portion. Preferably, the article includes a plurality of zones having different compressive forces that extend inwardly from the perimeter of the knitted article and which generally decrease from the first end to the second end. Still more preferably, the compressive forces have at least two different pressure gradient slopes with the pressure gradient slope nearer the first end being greater than the pressure gradient slope nearer the second end. In this manner, the knitted article provides a generally decreasing compressive force from the closed first end, which is adapted for a human foot, to the second open end, which is designed to terminate above the tibial plateau of a human leg. In some preferred embodiments of this aspect, the second end will terminate in the upper thigh area, nearer to the hip and in other embodiments, it will terminate at a point somewhere between the tibial plateau and the upper thigh area. Preferably, the knitted article is formed by circular knitting methods. In some forms, the knitted article includes at least one surface pattern on an outer surface of the knitted article. This surface pattern can be the same throughout the article or it can vary from the closed end to the open end. Still more preferably, the knitted article has a graduated compression density profile that simulates the human valve density profile throughout the human leg. Such a simulation is preferably accomplished by including a multiplicity of compression zones that decrease in compressive force inwardly from the circumference of the article, with a lower compressive force at the open end which increases in a slope-like fashion to a higher compressive force at the closed end of the article. Preferably there are no transition zones between the compression zones. In preferred forms, the compressive forces range from about 30 to 60 mm Hg near the closed first end and about 5 to 15 mm Hg near the closed second end. Again, the transition between the compressive forces is via a slope which decreases from the first end to the second end. In some forms, the decrease in compressive forces from the first end to the second end includes at least two different pressure gradient slope zones over the length of the article. Preferably, the compressive force pressure gradient slope is between about 2.5:1 to 3.5:1 from the first end to about the middle of the intervening portion and is about 1.5:1 to 2.5:1 from about the middle of the intervening portion to the second end. Preferably, the first end of the knitted article is adapted to surround a human leg from the toes to the ankle, the intervening portion is adapted to surround a human leg from the ankle to just above the tibial plateau and the third portion is adapted to surround a human leg from just above the tibial plateau to the upper thigh. In some preferred forms, the intervening portion includes at least two different compression gradient slope zones. Alternatively or additionally, in some forms, the intervening portion includes a greater number of zones having distinct pressure gradient slopes than said second end. One particularly preferred embodiment includes an intervening portion having a pressure gradient slope of about 3:1 and a second end having a pressure gradient slope of about 2:1.

In a fifth aspect of the present disclosure, a method of making a knitted article is provided. Generally, the method comprises the steps of: circular knitting a compressive article forming a seamless tubular article having a closed end and an open end, wherein the compressive force that extends inwardly from the circumference decreases from the closed end to the open end. In some preferred forms, there are no visibly detectable transition zones as the compressive force changes. In one variation of this aspect, the method includes the steps of: knitting at least one pattern visible on the outer surface of the knitted article.

In a sixth aspect of the present disclosure, a knitted compression hosiery article is provided. In general, the knitted article has a graduated compression density that simulates human valve density in the legs of an adult human. Preferably, the knitted article further includes patterns that selectively correspond to the compressive force strength that extends inwardly from a substantially circular cross section of the article. In one preferred form of this aspect, the article includes at least two zones of distinct compressive force each having a distinct pressure gradient slope that decreases from one end to the other. The article is adapted to be worn around a human leg with one of said zones extending from the ankle portion of the article to above the tibial plateau and the other of said zones extending from just above the tibial plateau to the upper thigh portion of the article.

These and other aspects of the present invention will become apparent to those skilled in the art after a reading of the following description of the preferred embodiment when considered with the drawings, as they support the claimed invention.

DETAILED DESCRIPTION

The present invention provides compression hosiery for improved vascular health including a knitted article having graduated compression density that simulates human vein valve distribution and functional effects in the legs.

Referring now to the drawings in general, the illustrations are for the purpose of describing a preferred embodiment of the invention and are not intended to limit the invention thereto.

Figure 1:
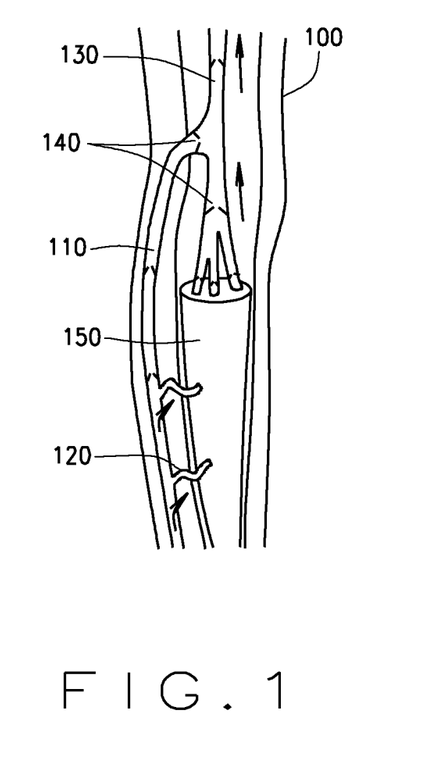
FIG. 1 illustrates the standard anatomic configuration of the superficial, deep, and perforating vein systems with the attendant valve functionality.

FIG. 1 is a schematic representation of normal venous return in the calf area of a leg 100. The venous return includes a superficial vein 110 leading to a deep vein 130 via a perforator vein 120. Both the deep vein 130 and superficial vein 120 include one-way valves 140, which act to prevent flow of blood toward the foot by closing when blood flow is urged downward by gravity or rest. As is known in the art, the calf muscle 150 acts as a pump when it contracts and such contraction urges venous blood upward, thereby opening the one-way valves to allow blood flow to pass therethrough.

Figure 2:
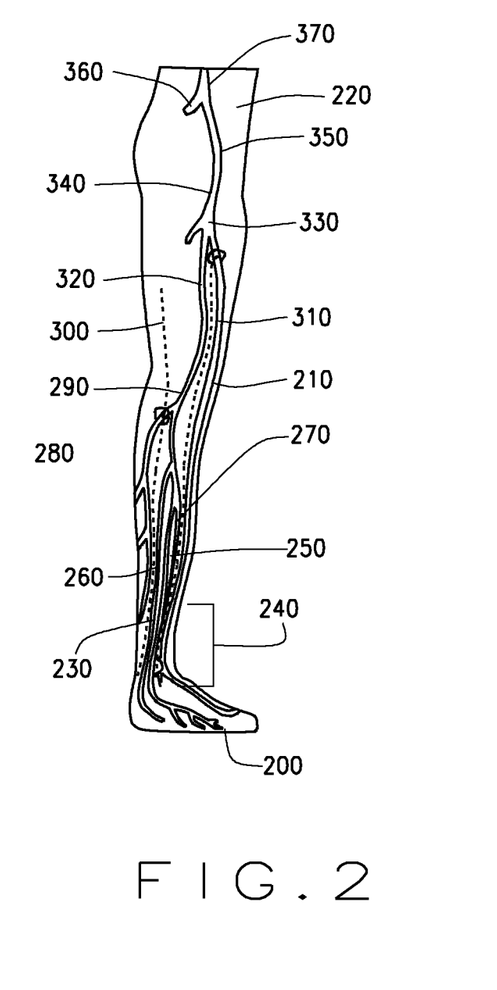
FIG. 2 is an illustration of the venous structure of a leg from the foot to the hip.

FIG. 2 is another schematic representation of the venous anatomy of a human leg. Beginning at the foot 200, there are internal perforating veins 240, lateral perforating veins 230, posterior tibial venae comites, anterior tibial veneae comites, the lesser saphenous vein, the popliteal vein 290 around the knee 210, deep fascia 300, the great saphenous vein 310, the superficial femoral vein 320, the common femoral vein 330, multiple valves 340, the external iliac vein 350, the internal iliac vein 360 and the common iliac vein 370.

Figure 3:
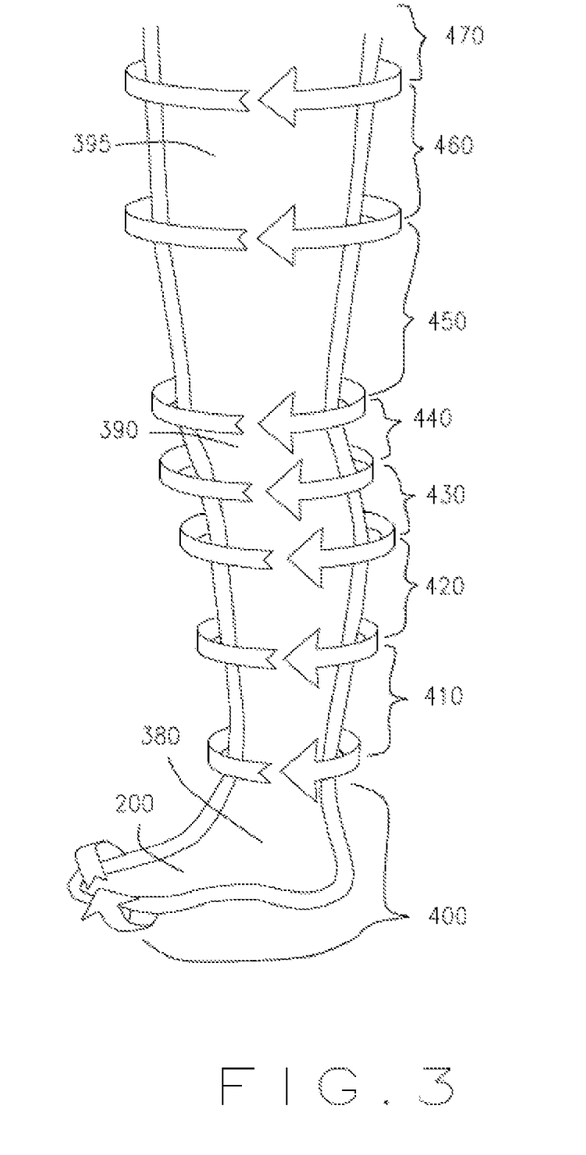
FIG. 3 is a schematic drawing of an embodiment of the present disclosure illustrating the different compression zones.
Figure 4:
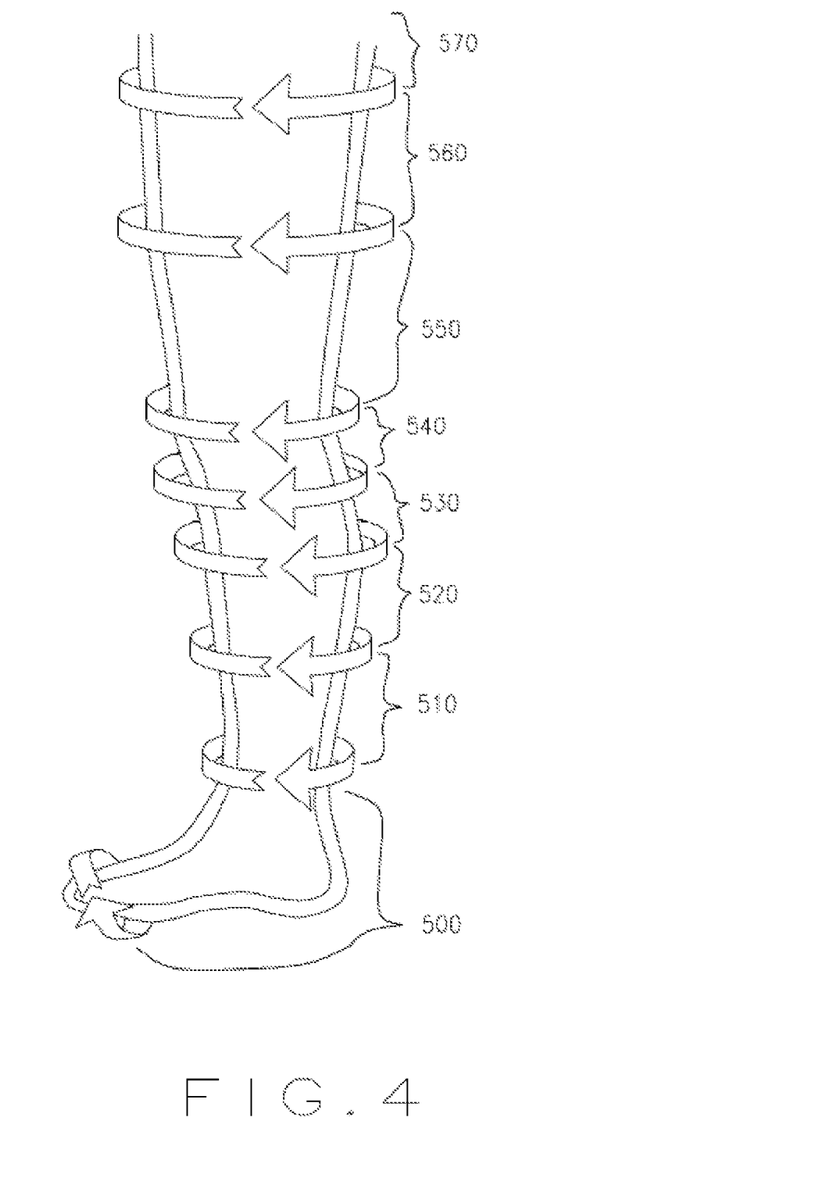
FIG. 4 is a schematic drawing of another embodiment of the present disclosure illustrating different compression zones.

FIGS. 3 and 4 are schematic representations of where different bands or zones of compression would be applied to a leg through a compression hosiery as described herein. From the foot 200, toward the ankle 380, toward the knee 390 and toward the thigh 395, bands or zones of decreasing compressive force contained in a compression hosiery will be applied to the leg of an individual. These bands or zones, 400, 500, 410, 510, 420, 520, 430, 530, 440, 540, 450, 550, 460, 560, 470, and 570 will apply circumferential pressure to the leg through the hosiery, thereby reducing the amount of blood that pools or collects in the venous system due to valvular incompetence. As can be appreciated, the zones or bands can have different lengths or widths, different compressive forces, and even vary in number as some compression hosiery will have two bands, and others will have three, four, five, six, seven, eight, nine, or more. Preferably, the compression hosiery will have a different slope of decreasing force below the tibial plateau (from the foot in the direction of the hip) than above the tibial plateau. Still more preferably, the slope below the tibial plateau will be steeper than the slope above the tibial plateau.

Figure 5:
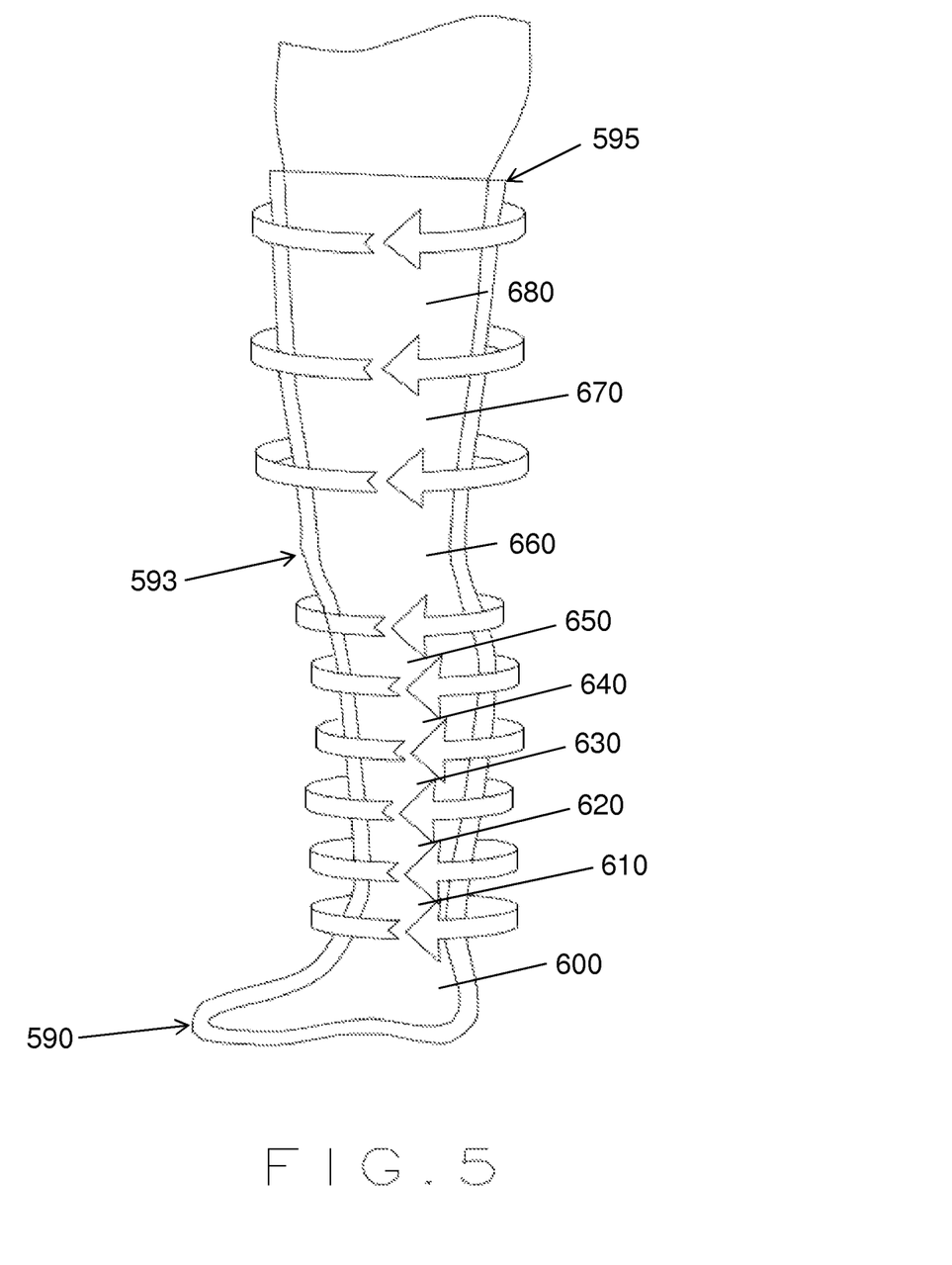
FIG. 5 is a schematic drawing of another embodiment of the present disclosure illustrating different compression zones wherein the compression hosiery extends to just below the hip.

FIG. 5 is a schematic illustration of a compression hosiery as described herein on a leg. As can be seen, the compression hosiery includes multiple bands or zones 600, 610, 620, 630, 640, and 650 that extend from the tip of the foot 590 past the knee 593 to just above the tibial plateau. There are also multiple bands or zones 660 and 670 that extend from just above the tibial plateau to the upper thigh or hip 595. As with the other embodiments described herein, each zone or band can have a different, discrete compressive force applied therein by the compression hosiery of the disclosure. Preferably, each zone or band has a gradient of pressure that generally decreases in a direction from the foot to the hip or increases in a direction from the hip to the foot. In some embodiments, the compression hosiery extends from the foot to just above the tibial plateau and in other embodiments, it extends past the tibial plateau to the hip, or any location therebetween. The number of bands or zones can vary as desired and can be customized for a particular individual based on physical characteristics, valvular location, medical condition, or other distinguishing feature. Even in embodiments that terminate just above the tibial plateau, there are at least two different zones having different compression gradient slopes.

In preferred embodiments, the knitted article having a compression knitted body is circular knitted, providing for the highest level of compression force at the lower portion of the knitted article, wherein the lower portion is constructed and configured to be worn on a human leg. Preferably, a foot portion is unitarily and integrally formed at the lower-most end of the article, with the opposite end remaining open for insertion of the foot therein. The compression force of the lower portion of the knitted article is greatest, and the knitted article is unitarily and integrally formed with a graduated decreasing compression force construction from the closed end to the open end. The compression slope between ankle and knee versus the slope of said change between knee and hip simulates the relative valve population differences between the two leg segments. As such, this compressive force slope is steeper between ankle and knee, than between knee and hip in a ratio approximating 3:1. Grossly, the total gradient from ankle to hip would still be one of decreasing compressive force.

The knitted article according to the present invention is preferably formed by methods of circular knitting, using circular knitting machines as known in the art enabled for making the article disclosed herein, such as by way of example but not limitation a 4-8 inch circular knitting machine.

In preferred embodiments, the knitted article is formed from a combination of at least two component yarn supplies. Preferably, at least one elastomeric and at least one non-elastomeric component are integrally combined in the circular knitting process to form a unitary and integral circular knitted article having a nonlinearly graduated compression density that recapitulates human valve density in the legs. More preferably, at least one visual pattern on the outer zone surface is provided wherein the visual pattern(s) do not correspond to the compressive force strength inwardly from the substantially circular cross section of the article, but provide for visually enhanced surface pattern(s), for example that provide slimming effect, sheer effect, or other aesthetically pleasing design, including but not limited to herringbone, chevron, asymmetrical or symmetrical patterns, and combinations thereof.

In any case, there are a multiplicity of pressure zones, preferably at least three zones from the toe end to the foot zone that is the closed end to the open end on the opposite end of the article as illustrated in the figures. Preferably, the compressive force inwardly from the circumference of the circular knitted article functions to provide the multiplicity of pressure zones that simulate the natural valve functionality for moving or stimulating blood flow upwardly toward the heart, in the direction of the open end of the knitted article and wherein there is no transition region between adjacent zones of compressive force in the unitarily and integrally circular knitted construction of the article according to the present invention.

Preferably, the materials selected for use in the kitted article are selected from synthetic materials, including nylon, polyester, elastomeric material, and combinations thereof, wherein the material combinations provide for a contributory component of the compression graduation in the article. In other embodiments, at least some of the materials or yarns used in the fabrication of the knitted article include natural fibers or blends of natural and synthetic fibers, such as by way of example and not limitation, cotton and elastomeric material.

Certain modifications and improvements will occur to those skilled in the art upon a reading of the foregoing description. The above-mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the present invention.

What is claimed is:

1. A knitted article comprising:
   a tubular body having a closed first end and an open second end connected by an intervening portion, wherein said article includes a plurality of zones having different compressive forces that extend inwardly from the perimeter of the knitted article and which generally decrease from the first end to the second end, wherein said compressive forces have at least two different pressure gradient slopes with the pressure gradient slope nearer the first end being greater than the pressure gradient slope nearer the second end, and wherein the compressive force pressure gradient slope is between about 2.5:1 to 3.5:1 from the first end to about the middle of the intervening portion and is about 1.5:1 to 2.5:1 from about the middle of the intervening portion to the second end.

2. The knitted article of claim 1, wherein the knitted article is formed by circular knitting methods.

3. The knitted article of claim 1, further including at least one surface pattern on an outer surface of the knitted article.

4. The knitted article of claim 3, wherein the surface pattern varies from the closed end to the open end.

5. The knitted article of claim 1, wherein said article has a graduated compression density profile that simulates the human valve density profile throughout the human leg.

6. The knitted article of claim 1, wherein there are a multiplicity of compression zones that decrease in a compressive force inwardly from the circumference of the article, with a lower compressive force at the open end and a higher compressive force at the closed end of the article.

7. The knitted article of claim 6, wherein there are no transition zones between the compression zones.

8. The knitted article of claim 1, wherein said compressive forces range from about 30 to 60 mm Hg near the closed first end and about 5 to 15 mm Hg near the closed second end.

9. The knitted article of claim 1, wherein the decrease in compressive forces from the first end to the second end includes at least three different pressure gradient slope zones over the length of the article.

10. The knitted article of claim 1, wherein said first end is adapted to surround a human leg from the toes to the ankle, the intervening portion is adapted to surround a human leg from the ankle to just above the tibial plateau and the third portion is adapted to surround a human leg from just above the tibial plateau to the upper thigh.

11. The knitted article of claim 10, wherein the intervening portion includes at least two different compression gradient slope zones.

12. The knitted article of claim 10, wherein said intervening portion includes a greater number of zones having distinct pressure gradient slopes than said second end.

13. The knitted article of claim 1, wherein said intervening portion has a pressure gradient slope of about 3:1 and said second end has a pressure gradient slope of about 2:1.

14. A method of making a knitted article comprising the steps of: circular knitting a compressive knitted article forming a seamless tubular article having a closed end and an open end with an intervening portion between the closed end and the open end, wherein the compressive force that extends inwardly from the circumference decreases from the closed end to the open end, and wherein the compressive force pressure gradient slope is between about 2.5:1 to 3.5:1 from the closed end to about the middle of the intervening portion and is about 1.5:1 to 2.5:1 from about the middle of the intervening portion to the second end.

15. The method of claim 14, wherein there are no visibly detectable transition zones as the compressive force changes.

16. The method of claim 14, further including the steps of: knitting at least one pattern visible on the outer surface of the knitted article.

17. A knitted compression hosiery article comprising: a knitted article having graduated compression density that simulates human valve density in the legs of an adult human, the knitted article further including patterns that selectively correspond to the compressive force strength that extends inwardly from a substantially circular cross section of the article.

18. The knitted compression hosiery article of claim 17, wherein said article includes at least two zones of distinct compressive force each having a distinct pressure gradient slope that decreases from one end to the other.

19. The knitted compression hosiery article of claim 18, wherein said article is adapted to be worn around a human leg and wherein one of said zones extends from the ankle portion of the article to above the tibial plateau and the other of said zones extends from just above the tibial plateau to the upper thigh portion of the article.

\* \* \* \* \*